US 009885650 B2

United States Patent
Yap et al.

(10) Patent No.: US 9,885,650 B2
(45) Date of Patent: *Feb. 6, 2018

(54) ACCELERATED LIFE TESTING DEVICE AND METHOD

(71) Applicant: Medtronic MiniMed, Inc., Northridge, CA (US)

(72) Inventors: Darren Y. K. Yap, Valencia, CA (US); Alexander E. Holmes, La Canada, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 89 days.

This patent is subject to a terminal disclaimer.

(21) Appl. No.: 14/997,252

(22) Filed: Jan. 15, 2016

(65) Prior Publication Data

US 2016/0131571 A1    May 12, 2016

Related U.S. Application Data

(63) Continuation of application No. 14/086,750, filed on Nov. 21, 2013, now Pat. No. 9,267,875.

(51) Int. Cl.
*G01N 17/00* (2006.01)
*H01L 21/67* (2006.01)

(52) U.S. Cl.
CPC ........... *G01N 17/002* (2013.01); *H01L 21/67* (2013.01)

(58) Field of Classification Search
CPC . H01L 21/67253; G01M 99/00; G01N 17/00; G01N 17/02
USPC ...................... 73/865.9, 866.52, 432.1, 865.6
See application file for complete search history.

(56) References Cited

U.S. PATENT DOCUMENTS

| | | | |
|---|---|---|---|
| 4,755,173 A | 7/1988 | Konopka et al. | |
| 4,995,273 A * | 2/1991 | Kisima | G01N 17/00 374/57 |
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |

(Continued)

*Primary Examiner* — Peter Macchiarolo
*Assistant Examiner* — Anthony W Megna Fuentes
(74) *Attorney, Agent, or Firm* — Medtronic MiniMed, Inc.

(57) ABSTRACT

An accelerated life testing device and method including an accelerated life testing method for a test piece within a test chamber, the method including: establishing a first atmosphere within the test chamber; changing the first atmosphere to a second atmosphere to form a deposition layer on the test piece; changing the second atmosphere to the first atmosphere to remove the deposition layer from the test piece; and repeating the changing the first atmosphere to the second atmosphere and the changing the second atmosphere to the first atmosphere to form an oxidation layer on the test piece.

20 Claims, 4 Drawing Sheets

(56) References Cited

U.S. PATENT DOCUMENTS

| | | | |
|---|---|---|---|
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2010/0160861 A1 | 6/2010 | Causey, III et al. |

\* cited by examiner

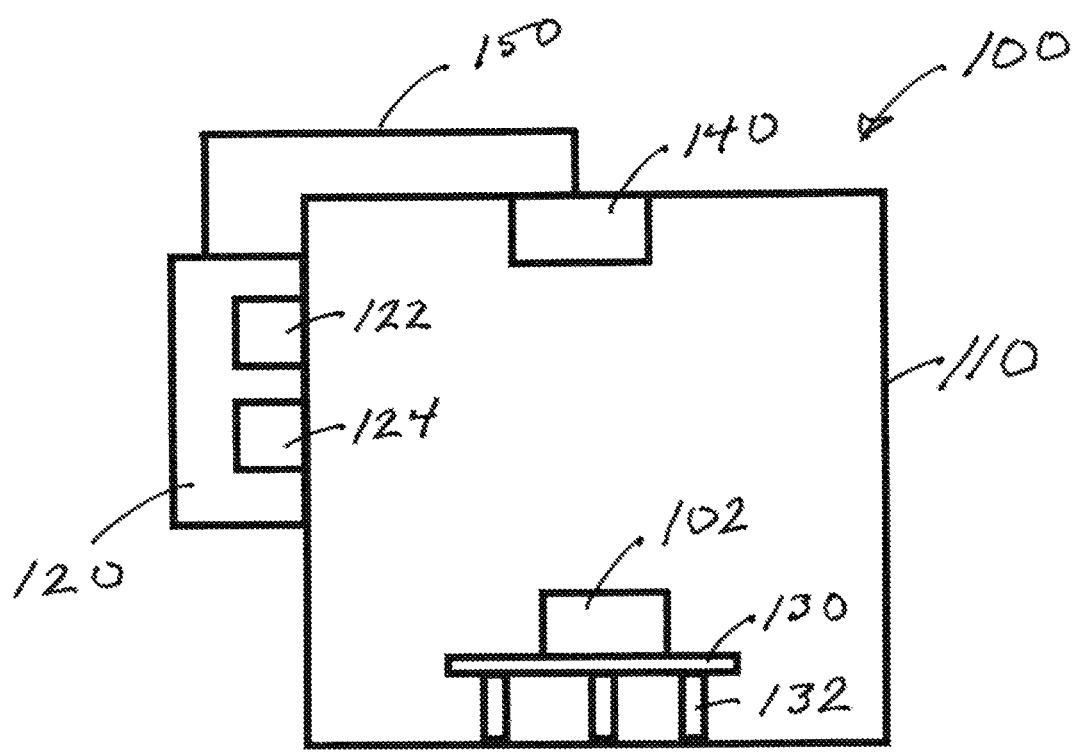

ACCELERATED LIFE TESTING DEVICE AND METHOD

RELATED APPLICATION

The present disclosure claims priority to and the benefit of U.S. patent application Ser. No. 14/086,750, filed on Nov. 21, 2013, the contents of which are hereby incorporated by reference in their entirety.

TECHNICAL FIELD

The technical field of this disclosure is qualitative testing devices and methods, particularly, accelerated life testing devices and methods.

BACKGROUND OF THE INVENTION

Highly Accelerated Life Testing (HALT) is a qualitative test method used to accelerate and identify failures in products, such as medical devices. The products are tested to failure to find failure modes and to identify the root causes of product and sub-system failures. Once failure modes and causes are identified, the product design can be improved to prevent or reduce the identified failures. The improved product design can then be retested to confirm that the identified failures are reduced. The HALT process results in rugged designs and high reliability products.

The HALT process can apply any stimulus to a product under test that can accelerate failure in the product, providing an indication of failures likely to occur in the field. One stimulus is temperature stress, which can be used in electronics testing to identify failures due to marginal components, poor timing margins, and poorly mounted heat sinks. Another stimulus is vibration, which can be used in mechanical and electronics testing to identify failures due to poor solder joints, loose hardware, and contact and wear between adjacent parts. Other stimuli used to accelerate failure can include general humidity, over-voltage, and over-current.

Unfortunately, present HALT processes are not able to provide a stimulus which accelerates oxidation in the product under test. Oxidation in the field normally occurs over a number of years, so failures in products in the field are too late to contribute to improved product design. The inability to accelerate oxidation during HALT processes prevents product design improvements from determining how oxidation affects the function of the device and identifying areas on which to focus design efforts. This, in turn, prevents achievement of highest product quality, product reliability, and patient safety.

It would be desirable to have an accelerated life testing device and method that would overcome the above disadvantages.

SUMMARY OF THE INVENTION

One aspect of the invention provides an accelerated life testing method for a test piece within a test chamber, the method including: establishing a first atmosphere within the test chamber; changing the first atmosphere to a second atmosphere to form a deposition layer on the test piece; changing the second atmosphere to the first atmosphere to remove the deposition layer from the test piece; and repeating the changing the first atmosphere to the second atmosphere and the changing the second atmosphere to the first atmosphere to form an oxidation layer on the test piece.

Another aspect of the invention provides an accelerated life testing device for use on a test piece, the device including: a test chamber for containing the test piece; and an atmospheric controller operably connected to the test chamber, the atmospheric controller being operable to control temperature and humidity within the test chamber. The atmospheric controller is operable to form an oxidation layer on the test piece by: establishing a first atmosphere within the test chamber; changing the first atmosphere to a second atmosphere to form a deposition layer on the test piece; changing the second atmosphere to the first atmosphere to remove the deposition layer from the test piece; and repeating the changing the first atmosphere to the second atmosphere and the changing the second atmosphere to the first atmosphere to form the oxidation layer on the test piece.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIG. 1 is a schematic diagram of an accelerated life testing device made in accordance with the invention.

DETAILED DESCRIPTION

Figure 2A:
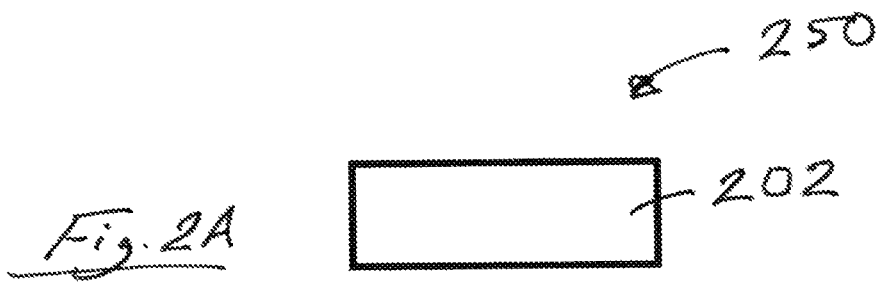
FIGS. 2A-2D are diagrammatic views of a test specimen undergoing accelerated life testing in accordance with the invention.

FIG. 1 is a schematic diagram of an accelerated life testing device made in accordance with the invention. Changing between a first atmosphere and a second atmosphere in the test chamber of the accelerated life testing device alternately forms and removes a deposition layer on the test piece, causing the surprising and unexpected result that an oxidation layer forms on the test piece.

The accelerated life testing device 100 is for use on a test piece 102. The accelerated life testing device 100 includes a test chamber 110 for containing the test piece 102 and an atmospheric controller 120 operably connected to the test chamber 110. The atmospheric controller 120 is operable to control temperature and humidity within the test chamber 110. The atmospheric controller 120 is operable to form an oxidation layer on the test piece 102 by establishing a first atmosphere within the test chamber 110; changing the first atmosphere to a second atmosphere to form a deposition layer on the test piece 102; changing the second atmosphere to the first atmosphere to remove the deposition layer from the test piece 102; and repeating the changing the first atmosphere to the second atmosphere and the changing the second atmosphere to the first atmosphere to form the oxidation layer on the test piece 102. The accelerated life testing device 100 can optionally include a vibration table 130 to which the test piece 102 can be secured and vibrated for testing response to vibration. The accelerated life testing device 100 can also optionally include atmospheric sensors and control systems to monitor and automatically control the atmospheric conditions within the test chamber 110.

The test piece 102 as defined herein can be any component or assembly of components to which a Highly Accelerated Life Testing (HALT) process is to be applied. In one embodiment, the test piece 102 can be a personal medical device, such as an insulin pump, a continuous glucose monitor, or the like. Other exemplary personal medical devices which can be used as a test piece 102 include pumps, cell pumps, heart-rate monitors, ECG monitors, pulse oximeters, blood pressure monitors, respiration rate monitors, skin temperature monitors, electroencephalography (EEG) monitors, activity level monitors, vital sign monitors, and the like. The surfaces of the test piece 102 on which the oxidation layer forms can be made of metal or any other material desired on which an oxidation layer can form.

The test chamber 110 can be any suitable enclosure for establishing an atmosphere around the test piece 102. In one embodiment, the test chamber 110 can provide a closed atmosphere, i.e., the test chamber 110 is sealed or substantially sealed from the outside environment so that gases and/or materials from the outside environment are not exchanged with test chamber 110. In another embodiment, the test chamber 110 can provide an open atmosphere, i.e., gases and/or materials from the outside environment are added to or removed from the test chamber 110.

The atmospheric controller 120 controls temperature and humidity within the test chamber 110, changing between a first atmosphere and a second atmosphere in the test chamber 110 to alternately form and remove a deposition layer on the test piece 102. This causes an oxidation layer to form on the test piece 102. The atmospheric controller 120 can be used for temperature stress testing and/or oxidation layer formation.

In one embodiment, the atmospheric controller 120 includes a temperature controller 122 and a humidity controller 124. The temperature controller 122 and the humidity controller 124 can be located within the test chamber 110, can communicate between the outside environment and the test chamber 110, or can be located within a loop through which air and/or other gases are withdrawn from and returned to the test chamber 110.

The temperature controller 122 can increase or decrease the temperature within the test chamber 110. Examples of temperature controllers include a liquid nitrogen source, a cold gas source, a hot gas source, a refrigeration coil, a heating element, and the like. The gas sources (liquid nitrogen source, cold gas source, hot gas source) introduce gases from the outside environment into the test chamber 110. The sealed sources (refrigeration coil, heating element) do not introduce material from the outside environment into the portion of the test chamber 110 including the test piece 102.

The humidity controller 124 can increase or decrease the humidity within the test chamber 110. Examples of humidity controllers include a water mister, a water drop injector, a dehumidifier, a desiccant, and the like. The humidity controller 124 can add moisture to or remove moisture from the atmosphere within the test chamber 110. The water sources (water mister, water drop injector) introduce water from the outside environment into the test chamber 110. The water removers (dehumidifier, desiccant) can condense or absorb moisture from the atmosphere within the test chamber 110.

The accelerated life testing device 100 can also optionally include an atmospheric sensor 140 to sense atmospheric conditions within the test chamber 110. The atmospheric sensor 140 can optionally generate an atmospheric signal 150 in response to the sensed atmospheric conditions, and the atmospheric controller 120 is responsive to the atmospheric signal 150 to control the atmospheric conditions within the test chamber 110. In one example, the atmospheric sensor 140 is a temperature sensor to sense the temperature within the test chamber 110. The temperature sensor can generate a temperature signal in response to the sensed temperature, and the atmospheric controller can be responsive to the temperature signal to control the temperature within the test chamber 110. In another example, the atmospheric sensor 140 is a humidity sensor to sense the humidity within the test chamber 110. The humidity sensor can generate a humidity signal in response to the sensed temperature, and the atmospheric controller can be responsive to the humidity signal to control the humidity within the test chamber 110. When the atmospheric controller 120 is responsive to the temperature signal and the humidity signal, the temperature signal and the humidity signal can be used separately or in combination to establish or change the atmospheric conditions within the test chamber 110.

The accelerated life testing device 100 can optionally include a vibration table 130 to which the test piece 102 can be secured for vibration testing. Pneumatic or electrodynamic actuators 132 can be used to move the vibration table 130 in the test chamber 110. Vibration testing can be applied simultaneously or sequentially with temperature stress testing and/or oxidation layer formation applied by the atmospheric controller 120.

FIGS. 2A-2D are diagrammatic views of a test specimen undergoing accelerated life testing in accordance with the invention. An oxidation layer forms on the test piece from alternately forming and removing a deposition layer on the test piece.

Referring to FIG. 2A, a test piece 202 is located within a first atmosphere 250 within a test chamber (not shown). In this example, the test piece 202 at the start of the accelerated life testing method is bare, without any oxidation layer.

Figure 2B:
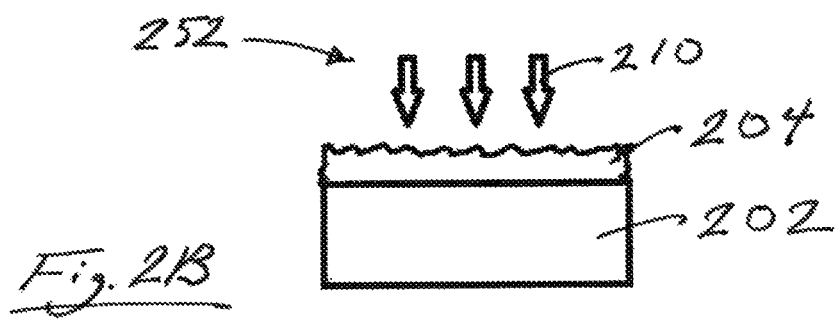

Referring to FIG. 2B, the first atmosphere is changed to a second atmosphere 252 to form a deposition layer 204 on the test piece 202. The arrows 210 illustrate the moisture coming from the second atmosphere 252 to form the deposition layer 204. In one embodiment, the temperature of the test piece 202 is below the dew point of the second atmosphere 252 and the deposition layer 204 is liquid water. In another embodiment, the temperature of the test piece 202 is below the frost point of the second atmosphere 252 and the deposition layer 204 is frost or ice.

Figure 2C:
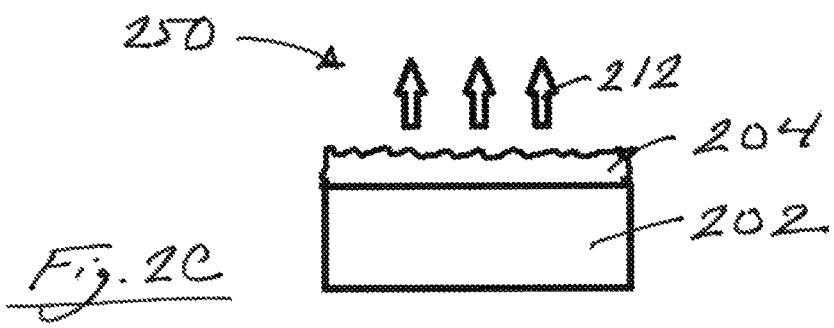

Referring to FIG. 2C, the second atmosphere is changed to the first atmosphere 250 to remove the deposition layer 204 from the test piece 202. The arrows 212 illustrate the moisture leaving the deposition layer 204 and entering the first atmosphere 250. In one embodiment, the deposition layer 204 is liquid water, which evaporates into the second atmosphere 252. In another embodiment, the deposition layer 204 is frost or ice, which melts into liquid water and runs off the test piece. In yet another embodiment, the deposition layer 204 is frost or ice, which melts into liquid water and evaporates into the second atmosphere 252 (dual phase removal). In yet another embodiment, the deposition layer 204 is frost or ice, which sublimates directly into the second atmosphere 252 (single phase removal). Those skilled in the art will appreciate that in another embodiment, the second atmosphere can be changed to another atmosphere different than the first atmosphere to remove the deposition layer 204.

Figure 2D:
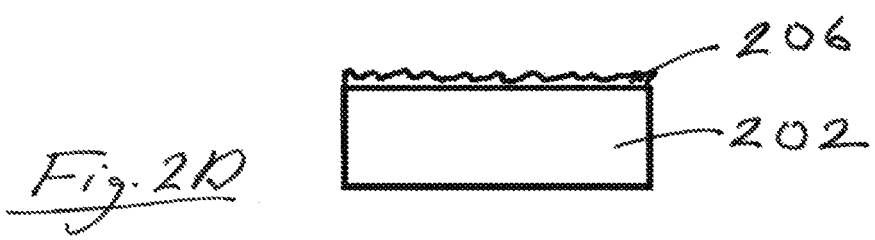

Referring to FIG. 2D, the deposition layer on the test piece has been alternately formed and removed a number of times by repeatedly changing between the first atmosphere and the second atmosphere, so that an oxidation layer 206 has formed on the test piece 202. The oxidation layer 206 introduces an additional failure mode when used in Highly Accelerated Life Testing (HALT). In one example, the oxidation layer 206 forms after the deposition layer on the test piece has been formed and removed approximately 10 times. In another example, the oxidation layer 206 forms after the deposition layer on the test piece has been formed and removed over several hours. In one experimental example as illustrated in FIG. 3, the oxidation layer 206 of copper oxide was formed on a printed circuit board made of FR4 fiberglass reinforced epoxy laminate: the oxidation layer was bluish white and non-conductive, and had a thickness between 0.1 and 35 micrometers.

Figure 3:
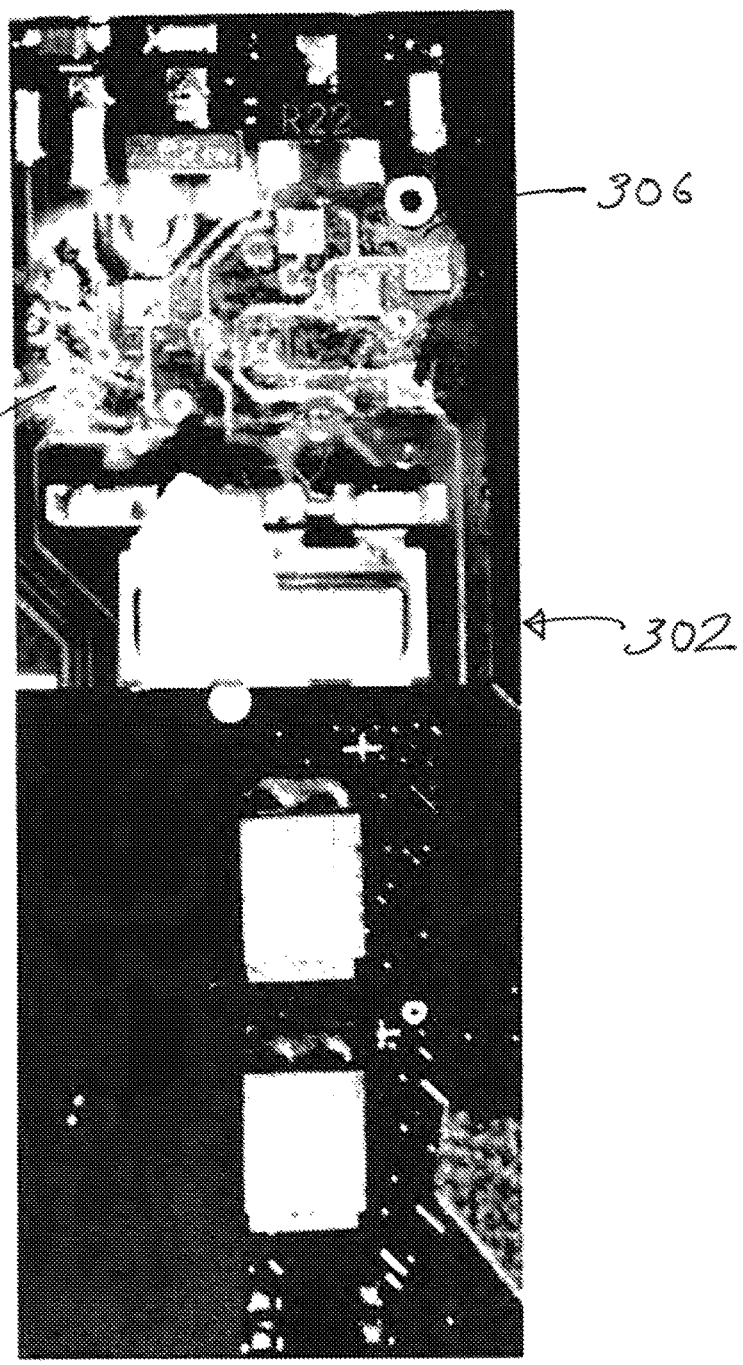
FIG. 3 is photocopy of a photograph of a test specimen showing oxidation structure from accelerated life testing in accordance with the invention.

FIG. 3 is photocopy of a photograph of a test specimen showing oxidation structure from accelerated life testing in accordance with the invention. In this example, the test piece is a printed circuit board 302 with an oxidation layer 306. The formation of the oxidation layer 306 on the circuit board 302 was a surprising and unexpected result. The oxidation layer 306 was formed by alternately placing the circuit board 302 in a first atmosphere at 70 degrees Centigrade and 0 percent humidity and a second atmosphere at −35 degrees Centigrade. The atmosphere was changed from the first atmosphere to the second atmosphere by admitting liquid nitrogen containing moisture into the test chamber. The atmosphere was changed from the second atmosphere to the first atmosphere by heating the inside of the test chamber with an electrically powered resistive heating element. The oxidation layer 306 formed after the deposition layer on the test piece had been formed and removed 10 times over several hours. The oxidation layer 306 was found to be made of copper oxide and have a thickness between 0.1 and 35 micrometers. As illustrated in FIG. 3, the oxidation area extended beyond the surface of the copper on the circuit board and extended onto the circuit board and nearby components.

Figure 4:
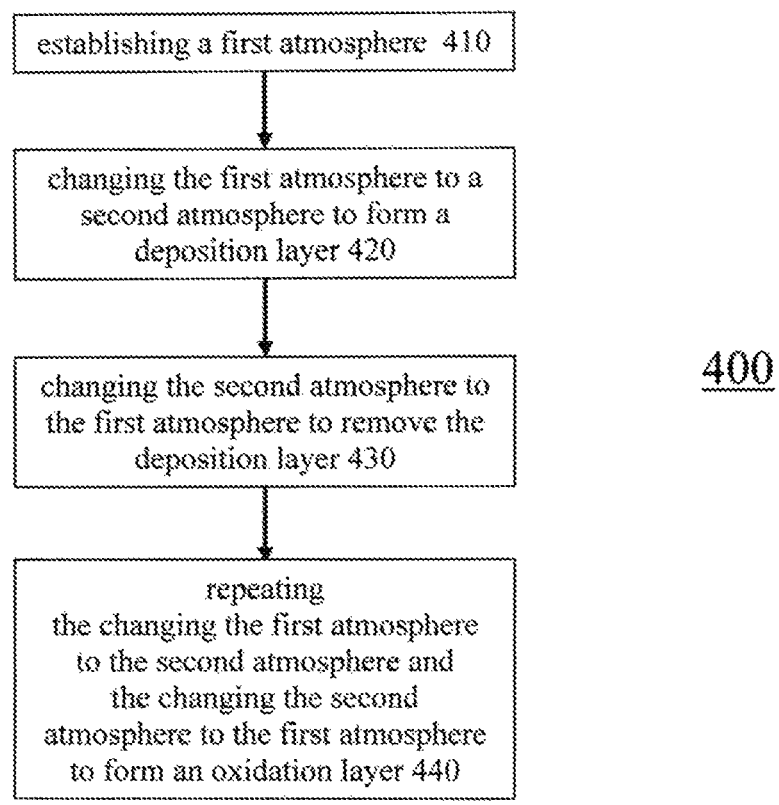
FIG. 4 is a flow chart of an accelerated life testing method in accordance with the invention.

FIG. 4 is a flow chart of an accelerated life testing method in accordance with the invention. The accelerated life testing method 400 for a test piece within a test chamber includes: establishing a first atmosphere 410 within the test chamber; changing the first atmosphere to a second atmosphere to form a deposition layer 420 on the test piece; changing the second atmosphere to the first atmosphere to remove the deposition layer 430 from the test piece; and repeating the changing the first atmosphere to the second atmosphere and the changing the second atmosphere to the first atmosphere to form an oxidation layer 440 on the test piece. The method 400 can optionally include vibrating the test piece.

The establishing a first atmosphere 410 within the test chamber includes establishing an atmosphere at a desired temperature and/or humidity. In one example, the first atmosphere is established at 100 degrees Centigrade and 0 percent humidity. In other examples, the temperature for the first atmosphere is in the range of 65 to 100 degrees Centigrade and in the range of 0 to 10 percent humidity.

The changing the first atmosphere to a second atmosphere to form a deposition layer 420 on the test piece can include decreasing the temperature within the test chamber, increasing the humidity within the test chamber, or a combination of decreasing the temperature within the test chamber and increasing the humidity within the test chamber. This can form a deposition layer of liquid water, frost, or ice. In one example, the second atmosphere is established at 50 degrees Centigrade. In other examples, the temperature for the second atmosphere is in the range of −30 to −60 degrees Centigrade. Those skilled in the art will appreciate that the conditions of the first atmosphere and the second atmosphere can be selected as desired for a particular application as required to form and remove the deposition layer.

The changing the second atmosphere to the first atmosphere to remove the deposition layer 430 from the test piece can include increasing the temperature within the test chamber, decreasing the humidity within the test chamber, or a combination of increasing the temperature within the test chamber and decreasing the humidity within the test chamber. The deposition layer can be liquid water, frost, or ice. When the deposition layer is liquid water, the deposition layer can evaporate. When the deposition layer is frost or ice, the deposition layer can sublimate, or melt to liquid water then evaporate from or run off of the test piece. Those skilled in the art will appreciate that the deposition layer can be partially or fully removed as desired for a particular application, i.e., a portion of the deposition layer can be left on the test piece and the next deposition layer formed on top of that portion of the deposition layer.

The repeating the changing the first atmosphere to the second atmosphere and the changing the second atmosphere to the first atmosphere to form an oxidation layer 440 on the test piece can be performed as many times or for as long as desired for a particular application. In one example, the oxidation layer forms after the deposition layer on the test piece has been formed and removed 10 times. In another example, the oxidation layer 206 forms after the deposition layer on the test piece has been formed and removed over several hours. In yet another example, the repeating continues for a predetermined number of 15 times, for a predetermined time of a few days, or until the test piece fails.

The method 400 can also include sensing an atmospheric condition within the test chamber, such as temperature, humidity, or a combination of temperature and humidity. The method 400 can also include controlling the atmospheric condition within the test chamber based on the sensed atmospheric condition.

The method 400 can optionally include vibrating the test piece. Exemplary vibrations can have a frequency of 6 to 10,000 cycles per second within acceleration parameters 5 to 80 gRMS with random vibration energy density profiles, as desired for a particular application.

It is important to note that FIGS. 1-4 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:
1. A qualitative testing device comprising:
  an enclosure suitable for establishing an atmosphere around a test piece; and
  an atmospheric controller operatively connected to the enclosure, the atmospheric controller operable to repeatedly change between atmospheres in the enclo- sure to alternately form and remove a deposition layer on the test piece, causing an oxidation layer to form on the test piece.

2. The qualitative testing device of claim 1, wherein the atmospheric controller further comprises at least one sensor and at least one control system that monitors and controls atmospheric conditions within the enclosure.

3. The qualitative testing device of claim 1, wherein the atmospheric controller further comprises a temperature controller operable to control temperature within the enclosure, and a humidity controller operable to control humidity within the enclosure.

4. The qualitative testing device of claim 3, wherein the temperature controller and the humidity controller are located within the enclosure or within a loop through which air or other gases are withdrawn from and returned to the enclosure.

5. The qualitative testing device of claim 1, wherein the test piece comprises at least one metal surface on which the oxidation layer forms.

6. The qualitative testing device of claim 1, wherein the enclosure further comprises a test chamber that provides a closed atmosphere that is substantially sealed from an outside environment.

7. The qualitative testing device of claim 1, wherein the enclosure further comprises a test chamber that provides an open atmosphere.

8. The qualitative testing device of claim 1, wherein the test piece further comprises a circuit board.

9. The qualitative testing device of claim 1, wherein the oxidation layer further comprises copper oxide.

10. A qualitative testing method comprising:
 alternately forming and removing a deposition layer on a test piece located in an enclosure by repeatedly changing an atmosphere within the enclosure; and
 forming an oxidation layer on the test piece as a result of the alternately forming and removing the deposition layer.

11. The method of claim 10, wherein the removing the deposition layer further comprises partially removing the deposition layer, wherein a portion of the deposition layer is left on the test piece; and forming a next deposition layer on top of the portion that is left.

12. The method of claim 10, wherein the repeatedly changing the atmosphere further comprises changing from a first atmosphere to a second atmosphere and changing from the second atmosphere to another atmosphere, wherein the another atmosphere is different than the first atmosphere.

13. The method of claim 10, further comprising sensing an atmospheric condition within the enclosure.

14. The method of claim 13, wherein the sensing the atmospheric condition further comprises sensing temperature, humidity, or a combination thereof.

15. The method of claim 13, further comprising controlling the atmospheric condition within the enclosure based on the sensing the atmospheric condition.

16. A method of accelerated life testing, the method comprising:
 forming a deposition layer on a test piece by changing a first atmosphere to a second atmosphere within a test chamber containing the test piece;
 removing the deposition layer from the test piece by changing the second atmosphere to another atmosphere;
 alternately forming and removing the deposition layer on the test piece by repeatedly changing between atmospheres; and
 forming an oxidation layer on the test piece from the alternately forming and removing the deposition layer on the test piece.

17. The method of claim 16, wherein the changing the first atmosphere to the second atmosphere further comprises setting a temperature of the test piece below a dew point of the second atmosphere, wherein the deposition layer is liquid water.

18. The method of claim 16, wherein the changing the first atmosphere to the second atmosphere further comprises setting a temperature of the test piece below a frost point of the second atmosphere, wherein the deposition layer is frost or ice.

19. The method of claim 16, wherein the changing the second atmosphere to another atmosphere further comprises changing the second atmosphere to the first atmosphere or to an atmosphere different than the first atmosphere.

20. The method of claim 16, wherein the forming the oxidation layer further comprises alternately forming and removing the deposition layer on the test piece for a predetermined number of times or for a predetermined duration.

* * * * *